United States Patent [19]

Margaron et al.

[11] Patent Number: 6,117,862

[45] Date of Patent: Sep. 12, 2000

[54] MODEL AND METHOD FOR ANGIOGENESIS INHIBITION

[75] Inventors: Philippe Maria Clotaire Margaron; Simon Leong, both of Burnaby; Julia G. Levy; Anna M. Richter, both of Vancouver, all of Canada

[73] Assignee: QLT, Inc., Japan

[21] Appl. No.: 09/169,735

[22] Filed: Oct. 9, 1998

[51] Int. Cl.$^7$ .............................. A01N 55/02; A61K 31/55
[52] U.S. Cl. ...................... 514/185; 514/253; 514/410; 514/455; 604/21
[58] Field of Search ..................... 514/410, 253, 514/455, 185

[56] References Cited

U.S. PATENT DOCUMENTS

| | | | |
|---|---|---|---|
| 4,577,636 | 3/1986 | Spears | 128/654 |
| 4,727,027 | 2/1988 | Wiesehahn et al. | 435/173 |
| 4,753,958 | 6/1988 | Weinstein et al. | 514/410 |
| 4,878,891 | 11/1989 | Judy et al. | 604/5 |
| 4,932,934 | 6/1990 | Dougherty et al. | 604/21 |
| 5,171,749 | 12/1992 | Levy et al. | 514/410 |
| 5,368,841 | 11/1994 | Trauner et al. | 424/9 |
| 5,756,541 | 5/1998 | Strong et al. | 514/502 |
| 5,770,619 | 6/1998 | Richter et al. | 514/410 |
| 5,776,966 | 7/1998 | North | 514/410 |
| 5,798,349 | 8/1998 | Levy et al. | 514/185 |
| 5,807,881 | 9/1998 | Leong et al. | 514/410 |

OTHER PUBLICATIONS

Abstract No. XP–002126043 of *Circulation Research* 76(2):161–167 (1995).

Abstract No. XP–002126044 of *Experimental Cell Research* 215(2):310–318 (1994).

Abstract No. XP–002126045 of 26th Annual Meeting of the American Society for Photobiology, Snowbird, Utah, USA, Jul. 11–15, 1998 American Society for Photobiology.

W. Gregory Roberts et al., "Role of Neovasculature and Vascular Permeability on the Tumor Retention of Photodynamic Agents," *Cancer Research* 52:924–930 (1992).

Enrique Mesri et al., "Expression of Vascular Endothelial Growth Factor from a Defective Herpes Simplex Virus Type 1 Amplicon Vector Induces Angiogenesis in Mice," *Circulation Research* 76(2):161–167 (1995).

Jasminka Vukanovic et al., "Antiangiogenic Effects of the Quinoline–e–Carboxamide Linomide," *Cancer Research* 53(8):1833–1837 (1993).

*Primary Examiner*—Dwayne C. Jones
*Attorney, Agent, or Firm*—Morrison & Foerster

[57] ABSTRACT

The invention provides a method to inhibit the formation of neovasculature while maintaining viability of the underlying tissue by subjecting a subject in which angiogenesis is to be inhibited to sublethal photodynamic therapy. The invention also provides a model for assessing sublethal PDT protocols to inhibit angiogenesis in particular target tissues.

16 Claims, 2 Drawing Sheets

```
//MacroMessage("Please Open Image File for Analysis.");
//OpenImage();
//ZoomFactor=-2
MacroMessage("Select ROI for Analysis.");
SelectROI();
RunMacro("C:/PROGRAM FILES/OPTIMAS6/dialogs/corlocal.mac",);
LBC_bUnitsPixels = TRUE;
LBC_rTileSizeX = 16;
LBC_rTileSizeY = 16;
LBC_bManualThreshold = FALSE;
LBC_bForegroundIsBlack = TRUE;
LBC_nIgnoreExtremes = 0;
LBC_nMinMaxForeground = 1:75;
LBC_CorrectBackground();
CloseWindow ("Local Smoothing and Thresholding");
LineCNVFactors[4:5] = 0.0 : 10;
//ZoomFactor = -1;
Threshold();
CreateLine(, , TRUE);
iNum=
        Prompt("Enter '1' to accept current threshold.\n":
        "Enter '2' to adjust threshold.\n" : "Enter '3' to stop macro.\n",
        "INTEGER");
If (iNum == 1)
MultipleExtractAll (TRUE);
Else If (iNum == 2)
Threshold();
MultipleExtractAll (TRUE);
Else If (iNum == 3)
Pause();
MultipleExtractAll (TRUE);
SetExport (LnTotalTally, 1, TRUE);
SetExport (mLnLength, 1, TRUE);
SetExport (mArArea, 1, TRUE);
MultipleExtractAll (TRUE);
pLnSum = Sum(mLnLength);
pArArea = Sum(mArArea);
MacroMessage ("The total capillary length is:", pLnSum);
```

FIG. 1

Effect of Genistein on ECV304
Tube-Length and Viability after 48 hours

MODEL AND METHOD FOR ANGIOGENESIS INHIBITION

TECHNICAL FIELD

The invention is in the field of angiogenesis and its inhibition. More specifically, the invention relates to the use of photodynamic therapy to inhibit formation of new blood vessels.

BACKGROUND ART

Photodynamic therapy (PDT) was first suggested as a method to treat malignant tumors. In this method, the subject is administered a photoactive agent such as a porphyrin derivative or a phthalocyanine; the photoactive agent was believed to localize preferentially in tumor tissue. When the tumor tissue was then irradiated with light of appropriate wavelength and absorbed by the photoactive agent, the decay of the photoactivated drug results in the regeneration of the drug and destruction or impairment of the surrounding tissue.

The use of PDT in the treatment of tumors has been established for many years, beginning with the use of hematoporphyrin derivative (HPD, a mixture of porphyrins) and a more potent derivative of HPD (porfimer sodium) which is described in, for example, U.S. Pat. No. 4,932,934. In addition to the treatment of tumors, PDT has been used to treat atherosclerotic plaques as described in U.S. Pat. No. 4,577,636 and in the treatment of skin diseases as described in U.S. Pat. No. 4,753,958. PDT has also been used to eradicate pathogens from blood and body fluids as described in U.S. Pat. No. 4,878,891 and U.S. Pat. No. 4,727,027.

A particularly useful group of photosensitizers, designated the "green porphyrins," is described, for example, in U.S. Pat. No. 5,171,749, incorporated herein by reference.

PDT has been found effective, generally, in destroying and impairing areas of neovascularization, as described in U.S. Pat. No. 5,770,619 without the necessity for the photoactive agent homing to a targeted area. This has particular application in treatment of diseases of the eye, in particular, age-related macular degeneration as described in U.S. Pat. No. 5,798,349. Photodynamic treatment of the eye has also been found to improve vision as described in U.S. Pat. No. 5,756,541. Photodynamic therapy has also been found useful in inactivating selectively certain white blood cells, as described in U.S. Pat. No. 5,776,966 and as further described in U.S. Pat. No. 5,807,881. Photodynamic therapy has also been found useful to treat rheumatoid arthritis when provided locally to affected joints, as disclosed in U.S. Pat. No. 5,368,841. Transplant rejection is also minimized using this technique, as described in U.S. Ser. No. 08/759,318, which is allowed.

All of the foregoing patent documents are incorporated herein by reference.

Thus, PDT has been found useful in a variety of contexts, including treatment of conditions which involve neovascularization, inflammation, and immune responses. However, it has not heretofore been realized that PDT can prevent as well as treat neovascularization. Thus, PDT has now been found, as a result of the present invention, to be useful for treatment of conditions associated with unwanted neovascularization at much earlier stages than would previously have been thought.

DISCLOSURE OF THE INVENTION

The invention is based on the surprising ability of PDT to inhibit neovasculature formation, as opposed to destroying or impairing existing neovasculature under conditions that maintain viability of the cells. This permits the use of PDT in treatment protocols designed and based on earlier treatment than would otherwise have been considered useful. Thus, for example, treatment of age-related macular degeneration (AMD) would be begun at a much earlier time.

Thus, in one aspect, the invention is directed to a method to inhibit the formation of neovasculature in a subject which method comprises administering to said subject a photoactive compound and irradiating the target portion of the subject in which neovasculature formation is to be prevented with a wavelength of light absorbed by the photoactive compound whereby the formation of neovasculature in this target area is inhibited, wherein the concentration of photoactive agent and time and intensity of radiation are such that the tissue in which said neovasculature is prevented remains viable. Specific indications in which such target areas are found include the choroid for prevention of AMD and areas of potential blood vessel concentration in forming hemaangiomas. The treatment is useful as well to prevent neovasculature in the iris, the retina and the cornea.

BRIEF DESCRIPTION OF THE DRAWINGS

FIG. 1 shows a customized macro to analyze the image of tubule formation.

MODES OF CARRYING OUT THE INVENTION

Figure 2:
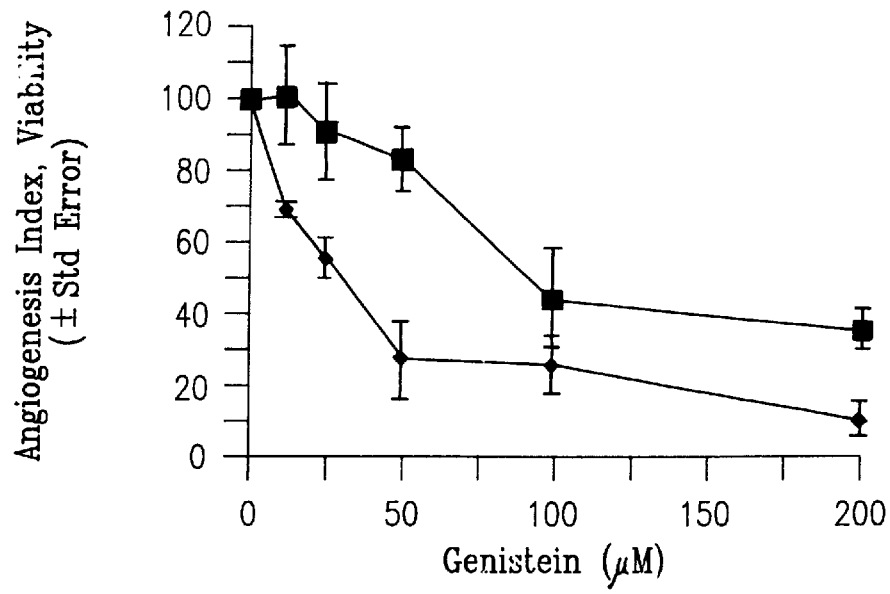
FIG. 2 is a graph showing the effect of genistein on ECV304 angiogenesis and viability.

The invention provides methods of treatment based on the discovery that PDT inhibits the formation of neovasculature, under conditions wherein viability of the underlying tissue is maintained.

This is verified by use of a model system wherein a culture of endothelial cells, preferably a cell line, is cultured in essentially two dimensions on a matrix support so that tubule formation can be observed directly. Typically, the matrix support is coated on a two-dimensional surface and precultured cells are plated onto the matrix. A preferred endothelial cell line is the human umbilical vein cell line (ECV304) available from the ATCC. A preferred matrix which can support the observable culture and formation of tubules is Matrigel® which is a solubilized basement membrane preparation extracted from mouse sarcoma and marketed by Becton-Dickinson (Bedford, Mass.). However, any endothelial cell culture and any suitable culture-supporting matrix can be used. The use of collagen gel support, for example, in supporting growth and proliferation, is well known.

The availability of a model system of this type and its use in evaluating photodynamic therapy are important because suitable protocols can be optimized so as to prevent angiogenesis and maintain viability in a straightforward manner. Cells representing the tissue to be treated, such as cornea, retinal cells, choroid, or any other tissue in which neovascularization is to be prevented can be used as the test tissue. The parameters suitable for any desired photosensitizer can also be verified in this manner.

The advantage of the present invention is that neovasculature can be prevented under photodynamic therapy conditions wherein the viability of the tissue in which the neovasculature is to be prevented is maintained. Thus, the treatment conditions must be modulated so that a sublethal effect on the tissue is maintained while a barrier to neovasculature formation is obtained. In general, the parameters which control this outcome are the nature and concentration of the photosensitizer, the intensity of the radiation absorbed by the photosensitizer, and the time of irradiation which, in combination with the intensity, determines the total light energy supplied. More powerful effects are obtained, of course, when the concentration of photosensitizer, intensity, and time of irradiation are increased. Decreases in one or more of these parameters permits increases in the remaining parameter or parameters.

As set forth above, the three basic parameters determining the lethality of treatment—i.e., parameters which determine whether viability can be maintained—are drug dose, power density (irradiance or fluence rate) and time of irradiation. In the present application, fluence rate is measured in $mW/cm^2$ and the product of this value times time provides energy in $J/cm^2$. In designing protocols, it is typical to consider drug dose and total light energy only, but fluence rate may also be important. If the fluence rate is too low, there is no sustained activation of the photosensitizer; if the fluence rate is too high, hyperthermic damaging effects occur. Also, in some protocols, the time of irradiation is a constraint and must be minimized. This is the case, for example, in the treatment of AMD and restenosis. Thus, in these protocols, the fluence rate will be higher than might otherwise be desirable.

A suitable balance of the relevant parameters can readily be obtained in the model system for the particular tissue to be targeted. The model system works, in general, as follows: The cells, plated onto the matrix support, are then maintained using medium suitable for the particular cell lines chosen. The cells are allowed to adhere to the matrix for a suitable time period before being subjected to a test protocol. The protocol may be employed prior to any visible formation of capillary-like tubes (CLT) or at any time before the formation of CLT is complete. Typically, the beginnings of tube formation can be observed after about 1–4 hours, but tubule formation is still incomplete after 24 or even 48 hours. Direct observation can be sufficient to provide a qualitative assessment of the ability of a test protocol to inhibit CLT, but it is preferable to quantitate the effect of the protocol using available computerized techniques. Images may be enhanced to correct irregular background lighting and measurement of capillary-like structures is made using a line tool, followed by image analysis using a customized macro. An exemplary macro is shown in FIG. 4.

Any protocol may be tested, then, using this model. Simple addition of compounds for inhibiting angiogenesis is easily performed. More complex protocols, such as PDT protocols, involve addition of a photoactive agent plus administration of light. A suitable control comprises the addition of genistein or any other compound known to inhibit angiogenesis.

By applying this model system, it has been found that photodynamic therapy is effective in inhibiting the progress of and the inception of angiogenesis without destroying the underlying tissue.

By "sublethal" photodynamic therapy is meant that the protocol kills less than about 50% of the population of treated cells, preferably less than 40%, more preferably less than 25%. Thus, the condition that the tissue or cells "remain viable" refers to the condition wherein less than 50% of the cells per se or cells contained in the tissue are killed by the treatment.

Suitable photoactive agents include porphyrin-based materials such as porfimer sodium, the green porphyrins, chlorin E6, hematoporphyrin derivative itself, phthalocyanines, etiopurpurins, texaphrin, and the like. Particularly preferred photoactive agents are the green porphyrins designated BPD-MA described, for example, in U.S. Pat. No. 5,171,749 referenced above, as well as EA6 and B3, described in U.S. Ser. Nos. 09/088,524 and 08/918,840, respectively, both incorporated herein by reference. Preferred green porphyrins have the basic structure:

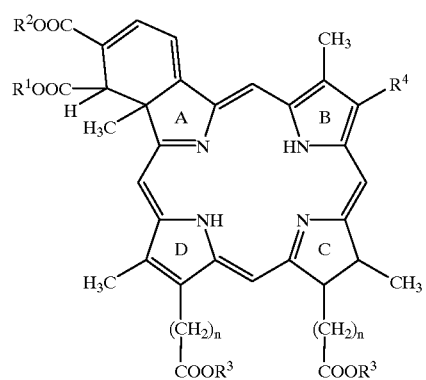

1 or

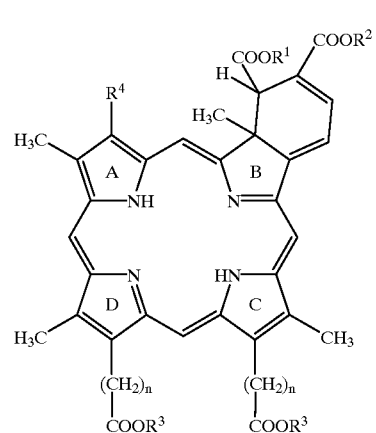

2 or

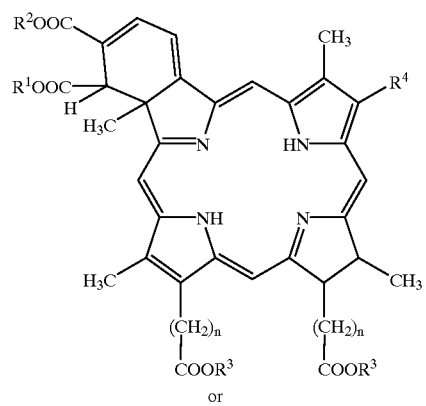

3

-continued

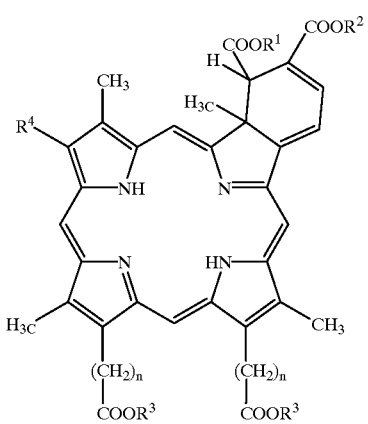

4 where $R^4$ is vinyl or 1-hydroxyethyl and $R^1$, $R^2$, and $R^3$ are H or alkyl or substituted alkyl.

BPD-MA has the structure shown in FIG. 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

Related compounds of formulas 3 and 4 are also useful; in general, $R^4$ will be vinyl or 1-hydroxyethyl and $R^1$, $R^2$, and $R^3$ are H or alkyl or substituted alkyl.

The radiation may be supplied through any convenient means appropriate to the performance of PDT. In the model system, the radiation is conveniently supplied simply by a standard light source such as a fluorescent bulb. For treatment of a subject, fiber optics or other more specialized means of delivery are preferred. The wavelength chosen will depend on the choice of photoactive compound; it will be apparent from the absorption spectrum of the photoactive agent what range of light will be suitable. The choice may also depend on the availability of a convenient light source.

The intensity and energy levels supplied are also dependent on the nature of the condition being treated. Typical levels of light energy are in the range of at least 1 $J/cm^2$. Photodynamic therapy may be conducted at traditional energy levels which may result in erythema as a side-effect, or may be conducted at "low dose" levels which are considered those equivalent to ambient light. For "ordinary" PDT, the light fluence generally varies between more than 50–200 $J/cm^2$. However, at "low-dose" levels, the fluence is typically less than that. Suitable low-dose levels may be determined by experimentally determining the level which first elicits the symptoms of erythema and then cutting the energy to one-fourth to one-sixth of that level. An explanation of "low-dose" PDT is found, for example, in U.S. Ser. No. 08/856,921 incorporated herein by reference. Briefly, low-dose PDT usually involves energies of less than 10 $J/cm^2$, preferably less than 5 $J/cm^2$, and more preferably 1 $J/cm^2$ or less. In the present application, however, somewhat higher energies may be desirable—for example, in the range of 25 $J/cm^2$. The energy can be supplied at a suitable rate with, in some instances, very low irradiation levels, on the order of 100 $\mu W/cm^2$ to 5 $mW/cm^2$. Again, in the present application, for sublethal PDT, somewhat higher intensities slightly less than 50 $mW/cm^2$ may be employed. As stated above, in order to maintain viability, the optimum balance between drug concentration, irradiation and time may be determined using a suitable model system such as that herein described. In general, however, the fluence rate and fluence is lower than that of traditional PDT. Traditional PDT employs higher total energies and higher fluences—energies on the order of 100–200 $J/cm^2$ and irradiances on the order of 200 $mW/cm^2$. Traditional PDT can be used to prevent neovasculature when viability is not an issue—for example, in treating tumors.

Since the application of PDT is able to inhibit the formation of capillaries—i.e., to inhibit angiogenesis, it is useful in the prevention and treatment of any condition that is characterized by unwanted angiogenesis. Such indications have been summarized in a number of reviews, including Pepper, M. S., *Arteriosclerosis, Thrombosis and Vascular Biology* (1997) 17:605–619, incorporated herein by reference, as well as Folkman, J., et al., *J Biol Chem* (1992) 267:10931–10934; Folkman, J., *New England Journal of Medicine* (1995) 333:1757–1763; and the use of antiangiogenic drug therapy for macular degeneration has been reviewed by Guyer, D. R., et al., *Seminars in Ophthalmology* (1997) 12:10–13. As described in the review by Pepper, prevention of angiogenesis is useful in a wide variety of indications involving many medical specialties, including prevention and treatment, vascular malformations, myocardial hypertrophy, hemaangiomas, pyogenic granuloma, Kaposi's sarcoma, glial tumors, and proliferative retinopathy as well as AMD. The method may also be used to prevent neovasculature in tumors, although under these circumstances, it is not necessary to regulate the dosage levels of photoactive compound and irradiation to maintain viability. Suitable protocols adapted to these conditions will be evident to those of skill in the art.

A major application for preventing neovasculature is in the area of treatment of the eye. As set forth in U.S. Pat. No. 5,798,349, traditional photodynamic therapy can be used to close the neovasculature associated with age-related macular degeneration (AMD). The sublethal photodynamic therapy described in the present application can then be used on a broader area of the choroid to prevent recurrence.

The following examples are intended to illustrate but not to limit the invention.

EXAMPLE 1

Effect of Genistein on Tubule Formation

As a control, to verify the validity of the model system used herein, and to provide a model based on which parameters for various photosensitizers can be determined, genistein, a known inhibitor of angiogenesis, was employed as a test protocol in the assay.

Endothelial cells for use in the assay were prepared as follows: The human umbilical vein endothelial cell line ECV304 (ATCC) was cultured in 75 $cm^2$ flasks (Falcon) using Medium 199 (M199, Sigma) supplemented with 2 mM 1-glutamine (Gibco BRL), 1 mM sodium pyruvate (Gibco BRL), 100 $\mu g/ml$ streptomycin (Gibco BRL), 20 mM HEPES (Sigma), and 10% heat-inactivated fetal calf serum (Gibco BRL). Cells were maintained at 37° C. in a humidified $CO_2$ (5%) chamber and subcultured at a ratio of 1:4 or 1:10 using 0.05% trypsin/0.005% EDTA (Gibco BRL) upon reaching confluence.

Matrigel® (Becton-Dickenson) was thawed for 2–3 hrs at 4° C. and then dispensed at 0.125 or 0.250 ml/well into plastic 24-well plates (Falcon). The gel was allowed to polymerize for at least 1 hr at 37° C. before the cells were applied.

For the assay, the ECV304 cells were plated onto 24-well plates coated with Matrigel® at a concentration of $3.5 \times 10^4$ cells/well. The cells were allowed to adhere to the Matrigel® coated plates for 24 hrs and then treated with various concentrations of genistein up to 200 µM. Images of CLT development were recorded after 48 hrs, converted to a digital format and analyzed using Optima 6.1 software, as illustrated in FIG. 1. Images were acquired with a Nikon camera coupled to a Zeiss Axiovert-35 microscope under bright-field illumination and converted into a digital format using the Hewlett-Packard Scan-Jet 4C/T. The summed length of CLT was quantified using the analysis software Optima 6.1. Viability was also assessed after 48 hrs using a standard MTT assay. The results both of antiangiogenic activity and viability are shown in Tables 1 and 2 and illustrated in FIG. 1.

TABLE 1

Effect of Genistein on ECV304 Tube-Length (% of Control) after 48 hours

| | Genistein (µM) | | | | | |
|---|---|---|---|---|---|---|
| Experiment No. | 0 | 12.5 | 25 | 50 | 100 | 200 |
| 1 | 100 | 41.19 | 31.62 | 10.70 | 2.31 | 3.32 |
| 2 | 100 | 81.81 | 57.11 | 30.47 | 49.73 | 20.82 |
| 3 | 100 | 77.86 | 39.82 | 24.15 | 9.54 | 6.37 |
| average | 100 | 68.81 | 55.53 | 27.00 | 25.40 | 10.17 |
| standard deviation | 0 | 23.93 | 23.16 | 14.86 | 23.73 | 9.35 |
| standard error | — | 13.82 | 13.37 | 8.58 | 13.70 | 5.40 |

TABLE 2

Effect of Genistein on Viability of ECV304

| | Genistein (µM) | | | | | |
|---|---|---|---|---|---|---|
| Experiment No. | 0 | 12.5 | 25 | 50 | 100 | 200 |
| 1 | 100 | 104.08 | 84.18 | 69.04 | 32.32 | 29.05 |
| 2 | 100 | 100.50 | 101.72 | 104.02 | 59.58 | 44.72 |
| 3 | 100 | 98.32 | 87.47 | 76.01 | 40.10 | 32.51 |
| average | 100 | 100.97 | 91.12 | 83.02 | 44.00 | 35.43 |
| standard deviation | 0 | 2.91 | 9.32 | 18.51 | 14.04 | 8.23 |
| standard error | — | 1.68 | 5.38 | 10.69 | 8.11 | 4.75 |

The results showed that genistein, as expected, at concentrations as low as 12.5 µM, inhibited angiogenesis substantially. Moreover, at concentrations of genistein up to about 25–50 µM, viability of the cells was not substantially affected.

EXAMPLE 2

Effect of PDT on Capillary-Like Tubule Formation

Endothelial cells for use in the assay were prepared as follows: The human umbilical vein endothelial cell line ECV304 (ATCC) was cultured in 75 cm² flasks (Falcon) using Medium 199 (M199, Sigma) supplemented with 2 mM 1-glutamine (Gibco BRL), 1 mM sodium pyruvate (Gibco BRL), 100 µg/ml streptomycin (Gibco BRL), 20 mM HEPES (Sigma), and 10% heat-inactivated fetal calf serum (Gibco BRL). Cells were maintained at 37° C. in a humidified $CO_2$ (5%) chamber and subcultured at a ratio of 1:4 or 1:10 using 0.05% trypsin/0.005% EDTA (Gibco BRL) upon reaching confluence.

Matrigel® (Becton-Dickenson) was thawed for 2–3 hrs at 4° C. and then dispensed at 0.125 or 0.250 ml/well into plastic 24-well plates (Falcon). The gel was allowed to polymerize for at least 1 hr at 37° C. before cells were plated.

ECV304 cells ($3.5 \times 10^4$ cells/well) were plated and allowed to adhere, differentiate and establish a capillary-like tube (CLT) network for 24 hours preceding treatment.

The photoactive compound, BPD-MA, liposomally formulated and reconstituted at 2.0 mg/ml in sterile distilled water, was added at various concentrations for 30 min. The plates were carefully washed twice with serum-supplemented M199 and then exposed to 1.0 J/cm² fluorescent red light (690 nm) provided by GE 15TA-R fluorescent tubes. The light was allowed to stabilize for 30 min, and then measured using a calibrated IL-1400 light meter. Pictures of CLT formation were obtained as described above 24 hrs after treatment with BPD-MA, using a Nikon camera coupled to a Zeiss Axiovert 35 microscope under bright field illumination. Once the images were converted into digital format using the Hewlett-Packard Scanjet 4C/T, the summed length of CLT was quantified using the analysis software Optimus 6.1 (Optimus Corp.). This software is illustrated in FIG. 1.

Viability was also determined. To assess cell viability, 96-well plates precoated with a thin layer of Matrigel® were reconstituted with 0.1 ml of M199 for a minimum of 1 hr at 37° C. as per the manufacturer's instructions. ECV304 cells ($8 \times 10^3$ cells/well) were placed in each well and incubated at 37° C. for 24 hours before exposure to the photodynamic protocol as set forth above. Approximately 24 hrs following treatment, viability was determined using the standard MTT assay. The results for both antiangiogenic activity and viability are shown in Tables 3 and 4 and in FIG. 3.

TABLE 3

Total Tube Length (% of Control) 24 hours post-PDT of 24 hour Culture of ECV304 on Matrigel ®

| | BPD-MA (ng/ml) | | | | | |
|---|---|---|---|---|---|---|
| Experiment No. | 0 | 12.5 | 25 | 50 | 100 | 200 |
| 1 | 100 | 70.18 | 85.93 | 20.42 | 31.08 | 18.80 |
| 2 | 100 | 65.11 | 83.73 | 76.07 | 23.06 | 10.71 |
| 3 | 100 | 98.47 | 62.34 | 49.32 | 37.04 | 19.95 |
| 4 | 100 | 74.06 | 50.00 | 23.82 | 46.93 | 5.19 |
| 5 | 100 | 80.68 | 63.85 | 75.28 | 12.47 | 7.36 |
| Average | 100 | 77.70 | 69.17 | 48.98 | 30.12 | 12.40 |
| standard deviation | 0 | 12.93 | 15.29 | 26.81 | 13.16 | 6.68 |
| standard error | — | 5.78 | 6.83 | 11.99 | 5.88 | 2.99 |

TABLE 4

Cell Viability (% of Control) 24 hours post-PDT of 24-hour Culture of ECV304 on Matrigel ®

| | BPD-MA (ng/ml) | | | | | |
|---|---|---|---|---|---|---|
| Experiment No. | 0 | 12.5 | 25 | 50 | 100 | 200 |
| 1 | 100 | 87.70 | 94.91 | 87.49 | 66.83 | 37.21 |
| 2 | 100 | 91.08 | 86.45 | 80.90 | 52.74 | 5.07 |
| 3 | 100 | 101.83 | 103.45 | 92.42 | 85.43 | 35.10 |
| 4 | 100 | 105.08 | 93.44 | 94.92 | 76.81 | 24.35 |
| Average | 100 | 93.54 | 94.94 | 87.60 | 68.33 | 25.79 |
| standard deviation | 0 | 8.34 | 6.98 | 6.62 | 14.04 | 14.70 |
| standard error | — | 4.17 | 3.49 | 3.31 | 7.02 | 7.35 |

As shown, angiogenesis was substantially inhibited at concentrations of 200 ng/ml of BPD-MA but viability was also diminished. However, angiogenesis was inhibited even at low concentrations of BPD-MA—between 25 and 100 ng/ml although cell viability was not substantially affected at these concentrations. The $LD_{50}$ (the dose that provides 50% cell death) was calculated to be 140 ng/ml while the dose required to prevent 50% CLT formation is approximately 50 ng/ml ($ID_{50}$=50 ng/ml).

Figure 3:
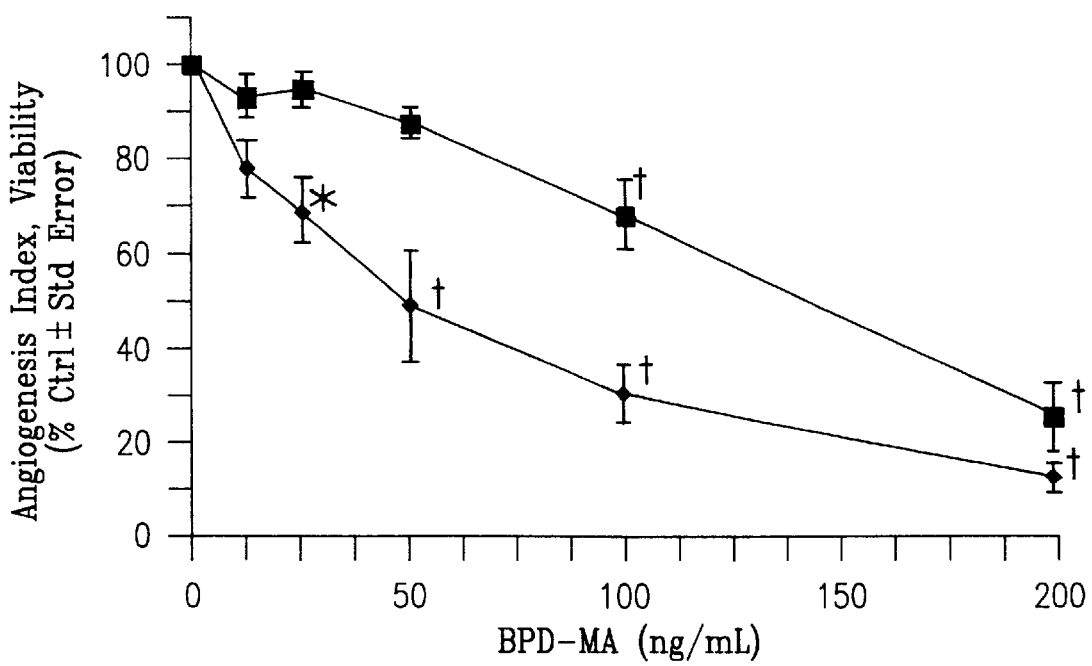
FIG. 3 is a graph showing the effect of PDT on ECV304 angiogenesis and viability 24 hrs after treatment.

These results are shown in graphic form in FIG. 3. Viability and angiogenesis index are plotted against concentration of BPD-MA in ng/ml. Solid squared represent viability and solid diamonds represent angiogenesis index. As seen, at 25–100 ng/ml, the effect on angiogenesis is much greater than on viability.

What is claimed is:

1. A method to prevent the formation of neovasculature in a target area of a subject which method comprises administering to a subject in need of said prevention a photoactive agent; and irradiating a target area in said subject in which said neovasculature formation is to be prevented with irradiation absorbed by the photoactive agent for a sufficient time and with sufficient intensity to inhibit formation of said neovasculature in said target area, wherein the concentration of photoactive agent and time and intensity of radiation are such that the tissue in which said neovasculature is prevented remains viable.

2. The method of claim 1 wherein the photoactive agent is a photoactivatable porphyrin-derivative.

3. The method of claim 2 wherein said porphyrin-derivative is porfimer sodium or is a green porphyrin.

4. The method of claim 3 wherein the green porphyrin is BPD-MA, EA6 or B3.

5. The method of claim 1 wherein the irradiation is at a total energy of less than 50 J/cm$^2$.

6. The method of claim 1 wherein said subject is at risk for pathologic conditions associated with ocular neovascularization.

7. The method of claim 6 wherein said subject is at risk for age-related macular degeneration (AMD).

8. A method to prevent the formation of neovasculature in a target area of a subject which method comprises irradiating said target area in a subject in need of such prevention with irradiation absorbed by a photoactive agent for a sufficient time and with sufficient energy to inhibit formation of said neovasculature in said target area, wherein said photoactive agent has been administered to said subject, wherein the concentration of photoactive agent and time and intensity of radiation are such that the tissue in which said neovasculature is prevented remains viable.

9. The method of claim 8 wherein the photoactive agent is a photoactivatable porphyrin-derivative.

10. The method of claim 9 wherein said porphyrin-derivative is porfimer sodium or is a green porphyrin.

11. The method of claim 10 wherein the green porphyrin is BPD-MA, EA6 or B3.

12. The method of claim 8 wherein said irradiation has an energy of less than 50 J/cm$^2$.

13. The method of claim 8 wherein said subject is at risk for pathologic conditions associated with ocular neovascularization.

14. The method of claim 13 wherein said subject is at risk for age-related macular degeneration (AMD).

15. A method to identify a protocol for a target tissue that inhibits angiogenesis while maintaining viability which method comprises:

providing a substantially two-dimensional culture of cells representing said tissue under conditions wherein said cells form tubules;

culturing a portion of the matrix and subjecting it to a test protocol;

culturing another portion of the matrix in the absence of a test protocol;

assessing the amount of tubule formation with respect to the first and second portions of the matrix and comparing the level of tubule formation in said portions; and assessing the viability of said first and second portions whereby a diminution in the level of tubule formation in the first portion, subjected to the test protocol, as compared to the second portion, cultured in the absence of the test protocol, and the percentage of viable cells in the first portion is at least half of the percentage of viable cells in the second portion, identifies the test protocol as inhibiting angiogenesis, while maintaining viability of the tissue.

16. The method of claim 15 wherein the supporting matrix supports tubule formation from endothelial cells.

* * * * *

UNITED STATES PATENT AND TRADEMARK OFFICE
CERTIFICATE OF CORRECTION

PATENT NO.  :  6,117,862

DATED        :  September 12, 2000

INVENTOR(S) :  Margaron, et al.

It is certified that error appears in the above-identified patent and that said Letters Patent is hereby corrected as shown below:

Under line [73] Assignee:  QLT Inc., "Japan" should be deleted and replaced with -- Vancouver, Canada--.

Signed and Sealed this

Twenty-fourth Day of April, 2001

Attest:

NICHOLAS P. GODICI

Attesting Officer         Acting Director of the United States Patent and Trademark Office